(12) United States Patent
Zychek

(10) Patent No.: US 6,252,202 B1
(45) Date of Patent: *Jun. 26, 2001

(54) FURNACE FOR HEAT TREATMENT OF DENTAL MATERIALS

(75) Inventor: George N. Zychek, Stratford, CT (US)

(73) Assignee: Jeneric/Pentron, Inc., Wallingford, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/243,985

(22) Filed: Feb. 4, 1999

Related U.S. Application Data

(60) Provisional application No. 60/074,246, filed on Feb. 10, 1998.

(51) Int. Cl.[7] .............................. A61C 13/20; F27B 17/02
(52) U.S. Cl. .................... 219/390; 219/385; 219/521; 373/112; 432/258; 432/135; 433/32
(58) Field of Search .................................. 219/390, 391, 219/420, 424, 476–480, 388, 541, 521, 385; 126/343.54; 164/34, 35, 246, 376; 264/16, 17, 19; 433/25, 32, 213; 432/229, 239, 241, 121, 253, 258, 135; 392/418; 373/115, 109, 112; 414/147, 153, 154, 172; A61C 13/20; F27B 17/02

(56) References Cited

U.S. PATENT DOCUMENTS

| | | | |
|---|---|---|---|
| 1,534,592 | * | 4/1925 | Houck .................................. 219/390 |
| 1,678,875 | * | 7/1928 | Rohn ................................... 219/390 |
| 1,818,789 | * | 8/1931 | Campbell ............................. 373/112 |
| 2,966,537 | * | 12/1960 | Witucki et al. ...................... 219/390 |
| 3,128,326 | * | 4/1964 | Hintenberger ....................... 373/112 |
| 3,441,652 | * | 4/1969 | Eicker ................................. 219/390 |
| 3,463,470 | * | 8/1969 | Green et al. ......................... 219/390 |
| 3,655,941 | * | 4/1972 | Schaun ................................ 219/390 |
| 3,694,122 | | 9/1972 | MacDonald et al. ................ 425/171 |
| 3,749,882 | | 7/1973 | Pilkington ............................ 219/390 |
| 3,859,041 | | 1/1975 | Winslow .............................. 432/250 |

(List continued on next page.)

FOREIGN PATENT DOCUMENTS

| | | |
|---|---|---|
| 2034893 | 1/1991 | (CA) . |
| 4303458 | * 1/1994 | (DE) . |
| 4302570 | * 3/1994 | (DE) . |
| 57-107026 | * 7/1982 | (JP) . |
| 1-91852 | * 4/1989 | (JP) . |
| 2-218117 | * 8/1990 | (JP) . |
| 8-322857 | * 12/1996 | (JP) . |

OTHER PUBLICATIONS

McPhee ER, "Hot Compressed Porcelain Process for Ceramo–Metal Restorations", pp. 245–250.

Primary Examiner—John A. Jeffery
(74) Attorney, Agent, or Firm—Ann M. Knab

(57) ABSTRACT

A furnace is provided generally including an upper heating chamber and a lower work base or firing platform. The upper chamber provides the main source of heat to the materials to be heat-treated. The upper chamber contains a muffle within which is located a heater ring assembly. The heater ring assembly is located in the middle to upper half of the muffle and includes an annular heating element that is located between an outer insulation ring and an inner quartz sleeve. A cavity or channel extends through the muffle into which insulation materials and the heater ring assembly is located. The channel area in the muffle below the heater ring assembly allows for the placement of the firing platform therein. The firing platform includes insulation material and a heating element located in the upper portion thereof. The heating element located in the firing platform provides heat to the firing platform such that when the firing platform is positioned within the muffle channel, heat is more evenly distributed throughout the heating area.

9 Claims, 6 Drawing Sheets

U.S. PATENT DOCUMENTS

| | | | |
|---|---|---|---|
| 3,860,738 | * | 1/1975 | Hintenberger ................... 219/390 |
| 4,114,024 | | 9/1978 | Donner ............................ 219/489 |
| 4,139,341 | | 2/1979 | Pfaffenbauer ................... 432/184 |
| 4,332,553 | | 6/1982 | Earle et al. ..................... 432/205 |
| 4,462,963 | * | 7/1984 | O'Brien et al. ................. 373/130 |
| 4,520,575 | | 6/1985 | Holmes et al. ...................... 34/23 |
| 4,702,696 | | 10/1987 | Bunza et al. .................... 432/205 |
| 4,760,044 | * | 7/1988 | Hokynar .......................... 219/390 |
| 4,828,490 | * | 5/1989 | Indig ................................ 432/124 |
| 4,943,234 | * | 7/1990 | Sohlbrand ....................... 432/152 |
| 4,950,870 | | 8/1990 | Mitsuhashi et al. ........... 219/390 |
| 4,976,613 | | 12/1990 | Watanabe ........................ 432/241 |
| 5,115,118 | | 5/1992 | Harada et al. .................. 219/390 |
| 5,128,515 | | 7/1992 | Tanaka ............................. 219/390 |
| 5,207,578 | | 5/1993 | Sakata ............................. 432/241 |
| 5,313,048 | * | 5/1994 | Berg et al. ...................... 219/390 |
| 5,432,319 | * | 7/1995 | Indig ............................... 219/390 |
| 5,498,292 | | 3/1996 | Ozaki .............................. 118/724 |
| 5,603,772 | | 2/1997 | Ide .................................. 118/724 |
| 5,645,419 | | 7/1997 | Ohsawa et al. ................. 432/241 |
| 5,702,514 | | 12/1997 | Petticrew ......................... 106/35 |

\* cited by examiner

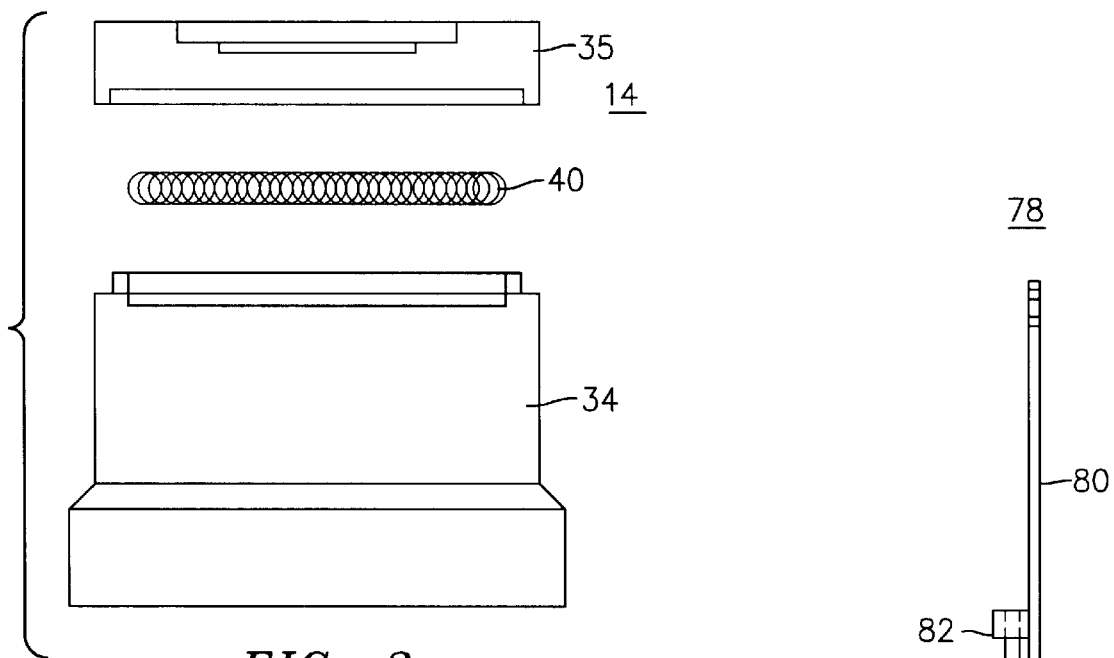
*FIG. 3*
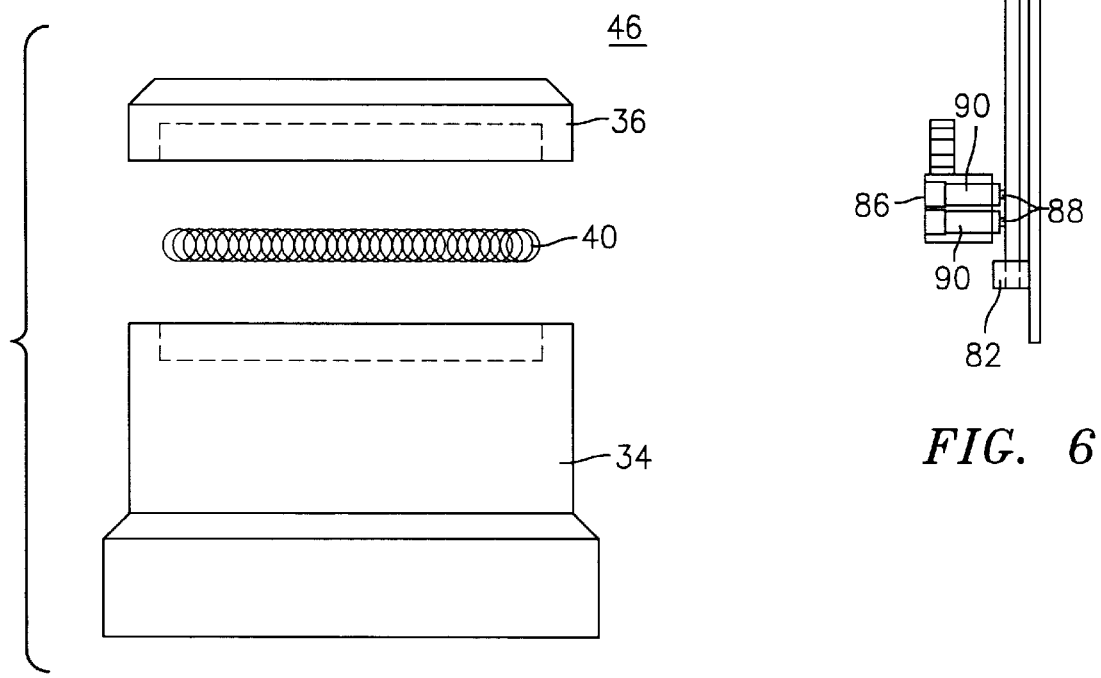
*FIG. 4*
*FIG. 6*

FURNACE FOR HEAT TREATMENT OF DENTAL MATERIALS

CROSS-REFERENCE TO RELATED APPLICATIONS

This application claims priority to U.S. Provisional Application No. 60/074,246, filed Feb. 10, 1998 which is hereby incorporated by reference.

FIELD OF THE INVENTION

This invention relates to a kiln, furnace or the like and more particularly to a furnace for use in firing and/or pressing of dental materials.

BACKGROUND OF THE INVENTION

Dental materials include porcelain facings, veneers, porcelain bridges, porcelain inlays, ceramic jacket crowns, all ceramic crowns, and a multitude of other porcelain dental products. Dental ceramics are typically fired in an inert environment such as in a vacuum atmosphere. Bottom loading furnaces can be used to heat treat the materials whereby the material to be heat treated is set on the lower shelf and is raised to an upper heating chamber for the heating process. Alternatively, a furnace, such as a pressing furnace, may have a stationary bottom shelf for placement of the material to be heat treated which may include the step of pressing the material into a desired form. In this type of furnace, the heating chamber is lowered over the material and the heating process commences. Although bottom-loading furnaces tend to have more uniform heating within the heating chamber than front loading furnaces, which experience cold spots at the front of the unit, nonuniform heating may still occur. The placement of the piece to be treated on the lower unheated insulation block may result in the occurrence of cool spots or insufficient predrying of the piece. As a result, longer soak times are required to heat the pressing mold and/or firing plate. Moreover, if the temperature distribution is uneven, workpieces treated in the same lot will be subject to variation in quality.

There remains a need to reduce cold spots in the furnace and provide uniform heating throughout the heating chamber of the furnace. It is desirable to provide a furnace for heating dental materials having a uniform heating atmosphere without compromising the efficiency and operation of the furnace.

SUMMARY OF THE INVENTION

These and other objects and advantages are accomplished in a furnace generally including an upper heating chamber and a lower work base or firing platform. The upper chamber provides the main source of heat to the materials to be heat-treated. The upper chamber contains a muffle within which is located a heater ring assembly. The heater ring assembly is located in the middle to upper half of the muffle and includes an annular heating element that is located between an outer insulation ring and an inner quartz sleeve. A cavity or channel extends through the muffle into which insulation materials and the heater ring assembly is located. The channel area in the muffle below the heater ring assembly allows for the placement of the firing platform therein. The firing platform includes insulation material and a heating element located in the upper portion thereof. The heating element located in the firing platform provides heat to the firing platform such that when the firing platform is positioned within the muffle channel, heat is more evenly distributed throughout the heating area. Cold spots which typically occur in the lower section of the heating area in conventional furnaces are reduced or eliminated in the furnace of the present invention due to the incorporation of the heating element in the firing platform. In one embodiment, the furnace of the present invention may be designed with the firing platform in the form of a stationary work base and the upper chamber movable from open to closed position. Accordingly, the furnace may be utilized as a pressing or porcelain furnace.

In an alternate embodiment, the furnace may be designed with the firing platform being movable from open to closed position. A movable firing platform in accordance with the present invention may include a linear support assembly that operates to move the firing platform into the muffle channel. A linear conductor assembly is also included to provide power to the heating elements. The linear conductor assembly includes copper conducting rods and a brush holder assembly that includes spring loaded brushes. The brushes maintain contact with the conducting rods to provide power to the heating elements without the inclusion of loose or stray wires. Accordingly, the possibility of the breakage of loose wires is reduced or eliminated by the incorporation of the linear conductor assembly.

BRIEF DESCRIPTION OF THE DRAWINGS

Features of the present invention are disclosed in the accompanying drawings, wherein similar reference characters denote similar elements throughout the several views, and wherein:

FIG. 3 is an enlarged view of the work base of the furnace shown in FIGS. 1 and 2;

FIG. 4 is an enlarged view of an alternative work base that may be used in the furnace of the present invention;

FIG. 6 is a partial view of the linear conductor assembly of the furnace of the present invention;

DETAILED DESCRIPTION OF THE INVENTION

Figure 1:
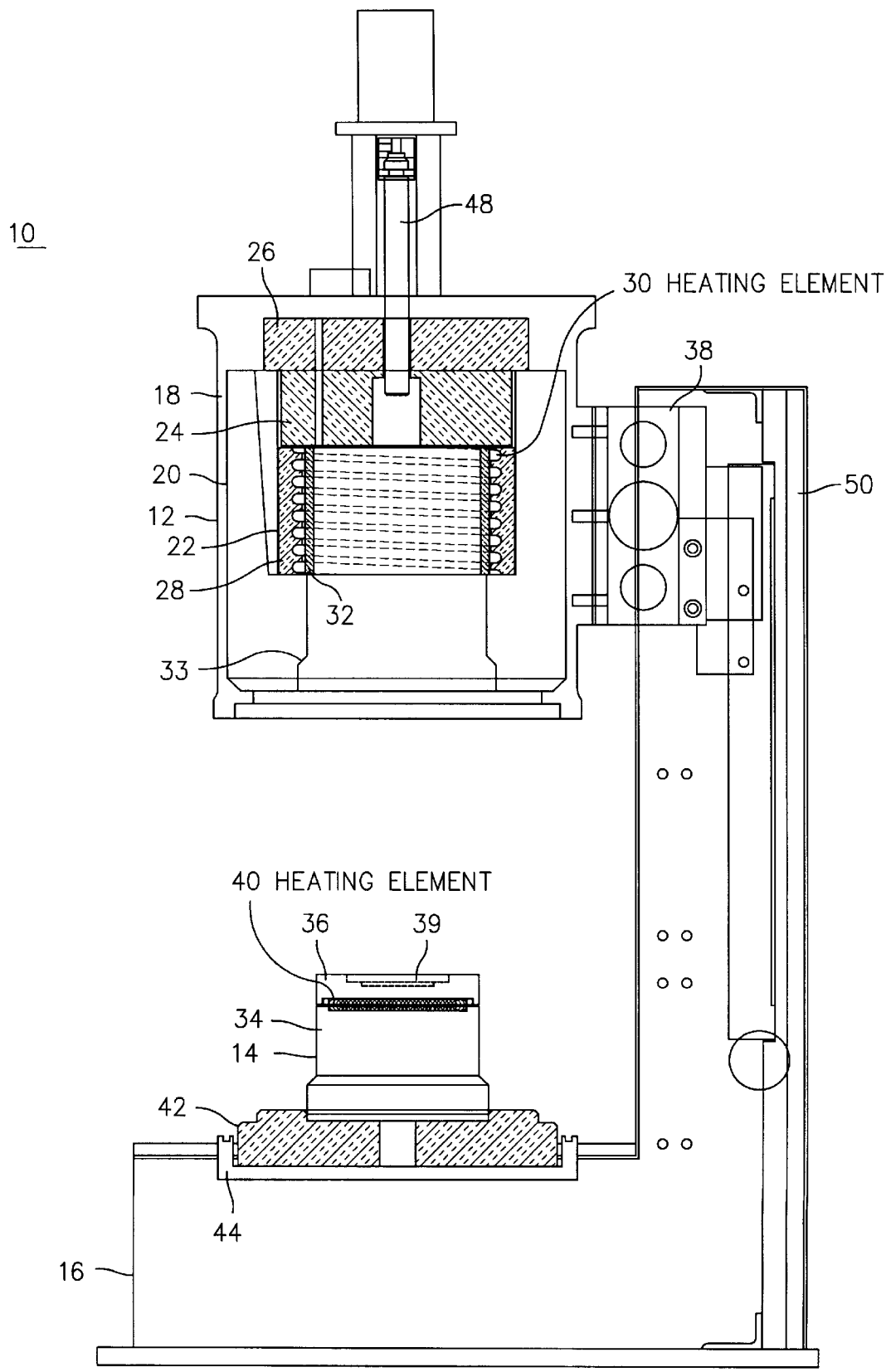
FIG. 1 is an elevational side view of the furnace of the invention in open position.

Turning to FIG. 1, an embodiment of a furnace 10 constructed in accordance with the present invention is shown with the understanding that those of ordinary skill in the art will recognize many modifications and substitutions which may be made to various elements.

Furnace 10 generally includes upper chamber 12 and lower work base or firing platform 14. Upper chamber 12 provides the main source of heat to the materials to be heat-treated. Firing platform 14 is located upon a support 16 that may include the control console for controlling the temperature and time of the heat treatment. Various electrical and vacuum line connections are at the back of the unit and are not shown. Heat treatment of the pieces to be treated may include but is not limited to pressing, molding, fusing and sintering.

Upper chamber 12 comprises an outer housing 18 preferably fabricated of aluminum or other similar material and a muffle member 20 which contains a heater ring assembly 22 and an insulation sleeve and cover, 24 and 26 respectively. Preferably, heater ring assembly 22 includes an outer insulation ring 28, an annular heating element 30 juxtaposed the inner wall of ring 28 and a quartz sleeve 32 disposed inward of heating element 30. Heating element 30 provides the main source of energy for heat treating the materials to be treated within channel or opening 33. Channel 33 extends through muffle 20 and is wider in the lower end to snugly fit firing platform 14 therein. The piece to be fired is positioned within quartz sleeve 32.

Firing platform 14 includes an insulation base 34 and a quartz cap 36 having indentations 39 therein for receiving a piece to be pressed. A heating element 40 is embedded within insulation base 34 proximate the top thereof. Heating element 40 is strategically located in base 34 to provide heat to the lower portion of the piece to be heat-treated. The placement of heating element 40 eliminates or reduces the formation of cold spots within channel 32 during the heating process. Firing platform 14 may be removable from an insulator plate 42 that is located on a housing plate 44 that is located on support 16. The insulation components in the muffle member and firing platform are preferably fabricated of a refractory material.

Figure 2:
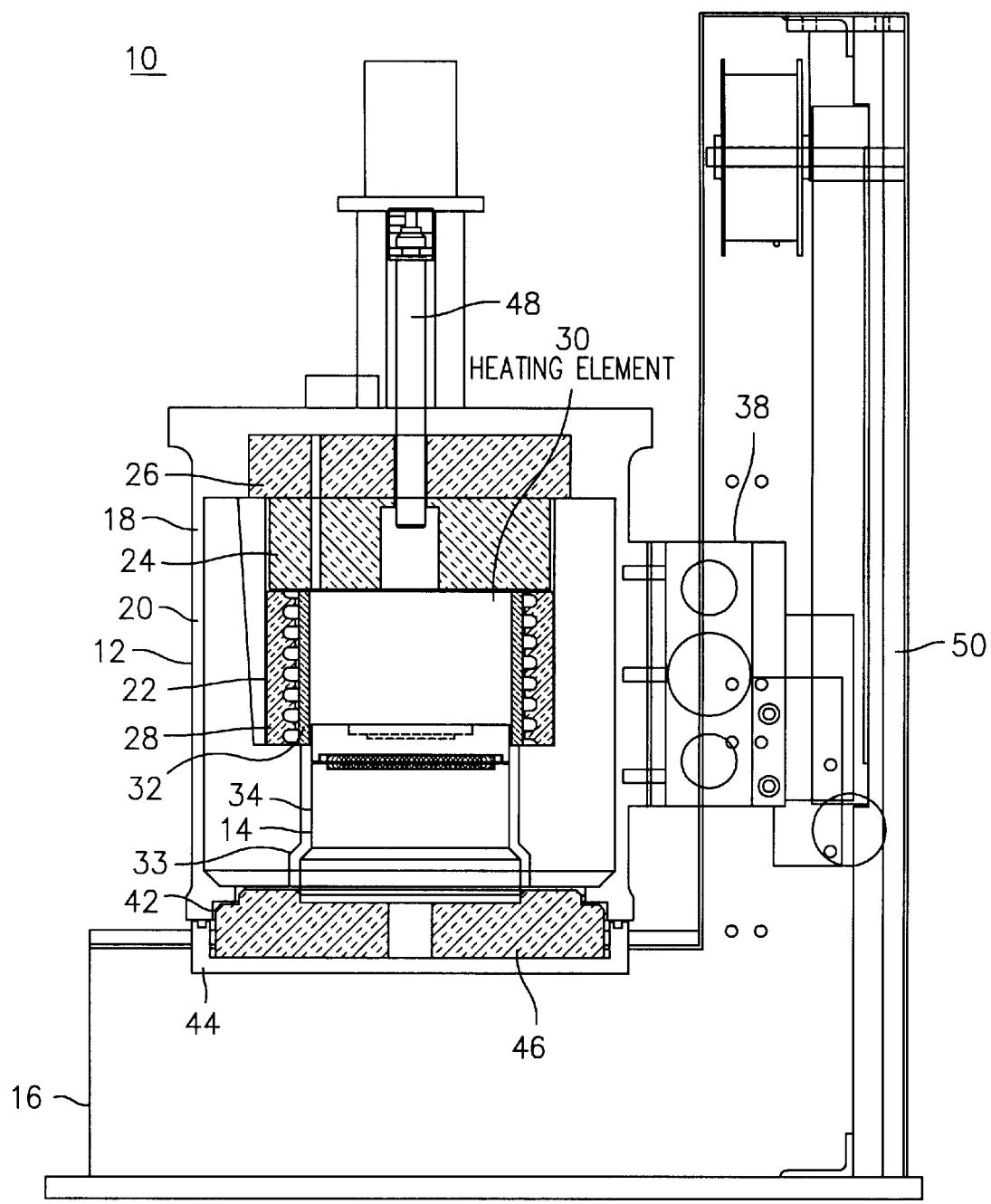
FIG. 2 is an elevational side view of the furnace in FIG. 1 shown in closed position.

In order to operate furnace 10, muffle 20 must be in closed position as shown in FIG. 2. Muffle 20 is movable from the upper to the lower position by bracket 38 which slides on stationary rail 50. Preferably, an inert atmosphere such as a vacuum atmosphere is provided within channel 33 through a slot located in insulator plate 42. When in closed position, muffle 20 is preferably sealed under vacuum and pressing is performed by piston 48 located in upper chamber 12. As shown in FIG. 2, firing platform 14 is of sufficient height to position the piece to be heat treated within the area primarily where heating element 30 is located.

FIG. 3 is an enlarged view of the firing platform 14 with insulation base 34, heating element 40 and quartz cap 35. Platform 14 is typically used when furnace 10 is utilized as a pressing furnace. The furnace may be heated to temperatures as high as 1200° C. The furnace may also be designed to include heating capabilities for porcelain firing. FIG. 4 depicts an alternate firing platform 46 that includes insulation base 34, heating element 40, and insulation cover 36. Platform 46 is typically used when pressing is not necessary and furnace 10 is used as a porcelain furnace. Heating element 40 may be a coil-shaped resistant heating element made of an alloy such as Fe—Cr—Al alloy, coiled in any shape and preferably formed like a ring. In FIGS. 3 and 4, heating element 40 is shown as being substantially parallel to the top of base 34 and also substantially parallel to cap 35 and cap 36, respectively, of firing platform 14 and firing platform 46, respectively.

Figure 5:
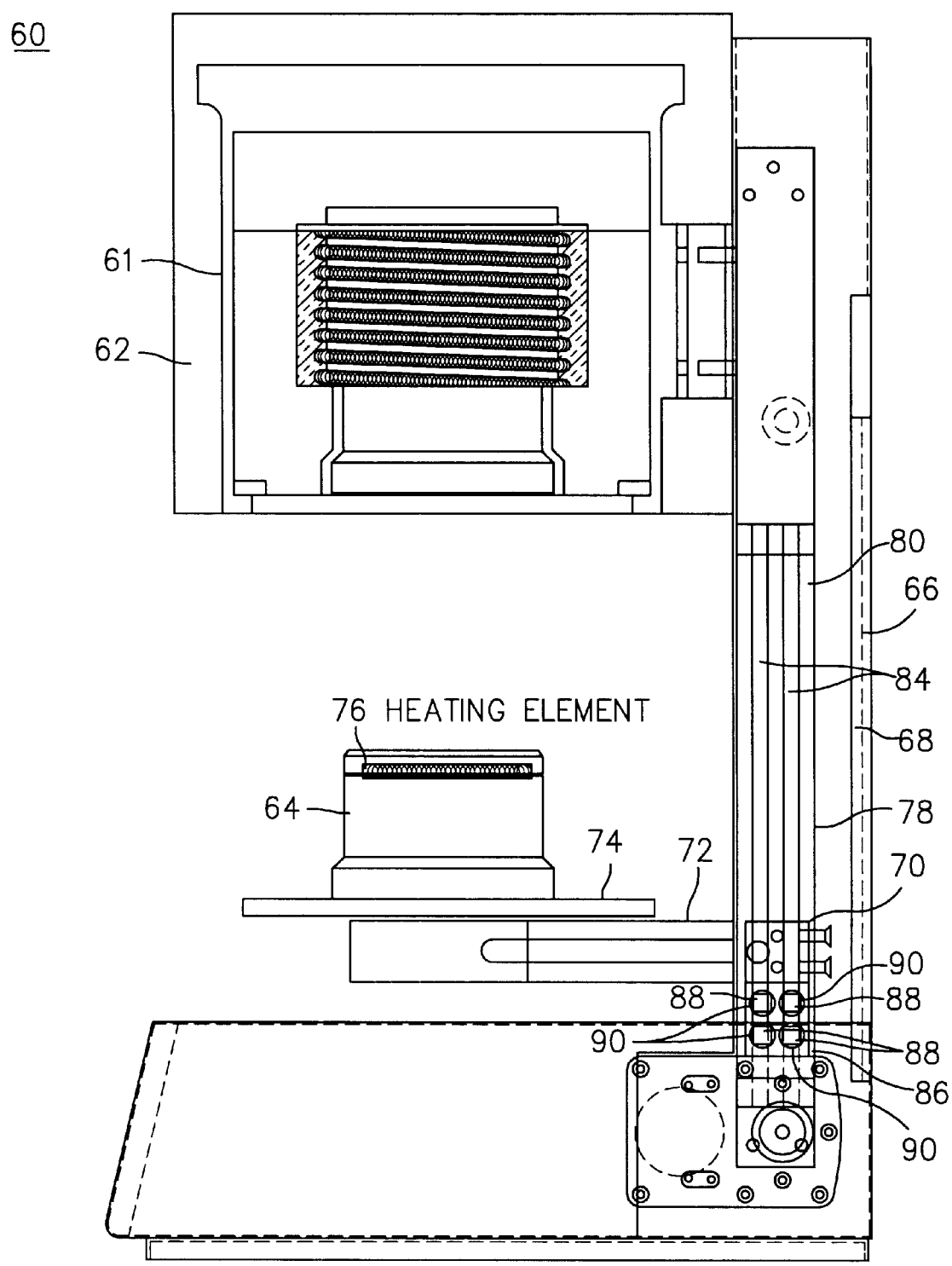
FIG. 5 is an elevational side view of the furnace of the present invention showing a movable work base.

FIG. 5 depicts an alternate embodiment of the invention. Furnace 60 may be used as a porcelain furnace for heating dental ceramic materials. Similar to furnace 10, furnace 60 includes an upper chamber 62 and a lower firing platform 64 along with the same or similar components therein as depicted in FIG. 1. During the operation of furnace 60, the ceramic piece or pieces to be fired are positioned on firing platform 64 and platform 64 is moved from a lower resting position to an upper position within upper chamber 62. Platform 64 may be movable by a linear support assembly 66. Linear support assembly 66 includes a mounting bar 68 which is stationary. A movable lift bracket 70 is preferably mounted to bar 68 by a ball bearing carriage. Further connected to bracket 70 is a work base 72 and a work base plate 74. Bracket 70 moves vertically on bar 68 and is powered by a conducting rail 80.

Figure 7:
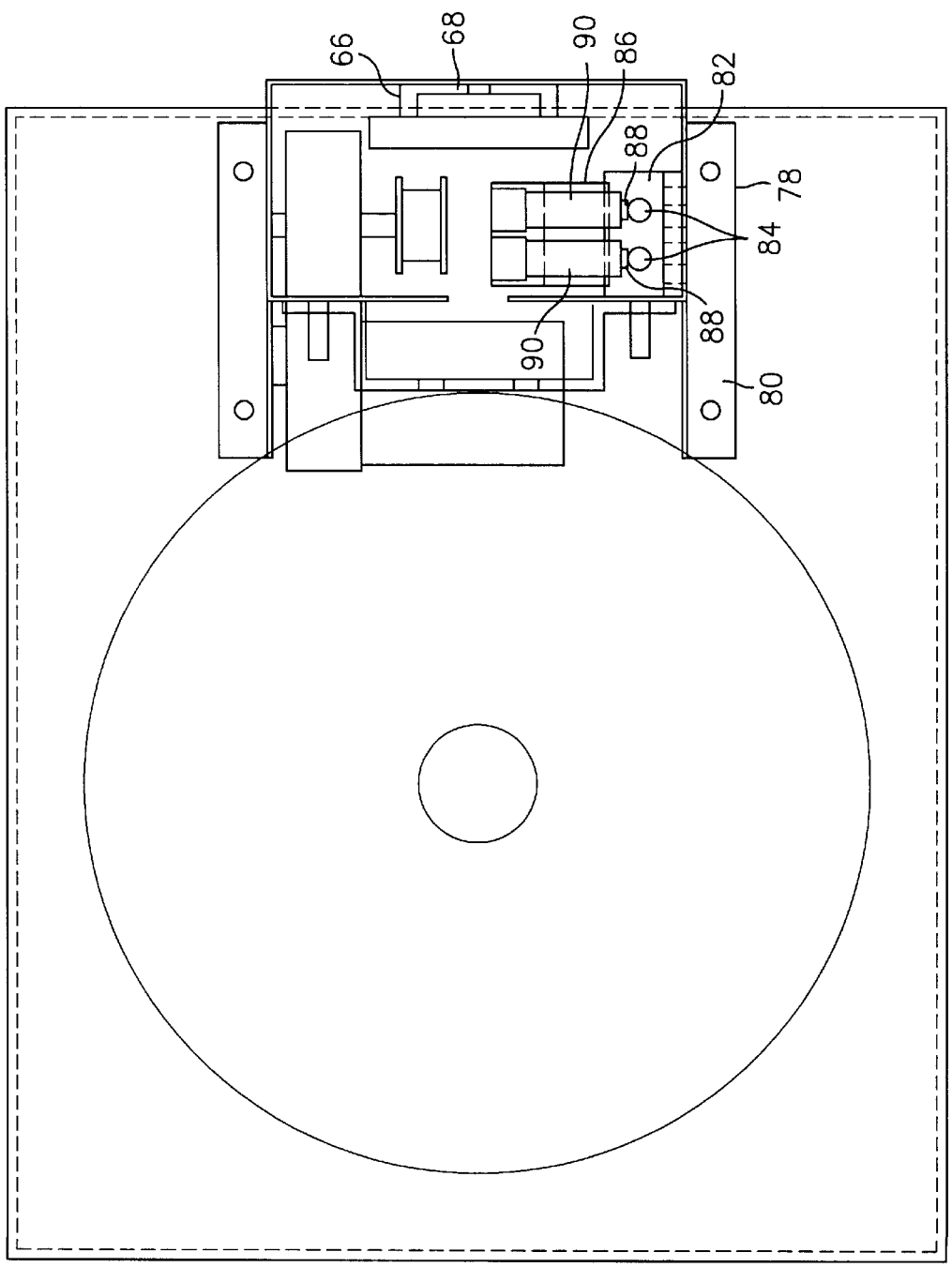
FIG. 7 is a top plan view of the linear support assembly of the furnace of the present invention.

The location of a lower heating element 76 in platform 64 requires connection to a power source within the furnace. A linear conductor assembly 78 is located within furnace 60 and connected to an internal power not shown. As clearly shown in FIGS. 6 and 7, linear conductor assembly 78 includes a conducting rail 80 to which is mounted insulator blocks 82. Attached to and located between insulator blocks 82 are copper conductor rods 84. A brush holder assembly 86 is mounted on linear support assembly 66 as shown in FIG. 5. Brush holder assembly 86 moves vertically as bracket 70 moves along rail 68. Brush holder assembly 86 includes spring loaded brushes 88 which maintain contact with conductor rods 84 as bracket 70 moves along bar 68. Brushes 88 are contained in brush holders 90. As a result, a power connection is maintained between the power source and lower heating element 76 as platform 64 moves along rail 68. Moreover, conducting rail 80 transfers electrical power through brushes 88 to linear support assembly 66 to move bracket 70 along bar 68. Linear conductor assembly reduces safety concerns regarding loose wires that could move and break during the movement of platform 64.

Figure 8:
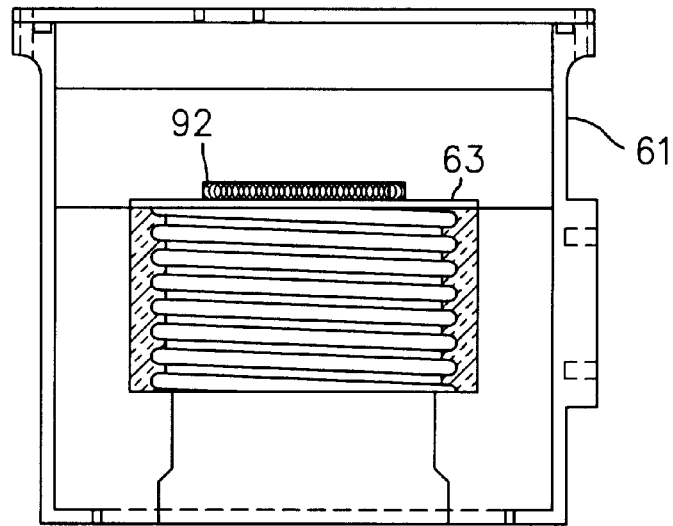
FIG. 8 is a cross-sectional view of a portion of the muffle member in the furnace shown in FIG. 5.
Figure 9:
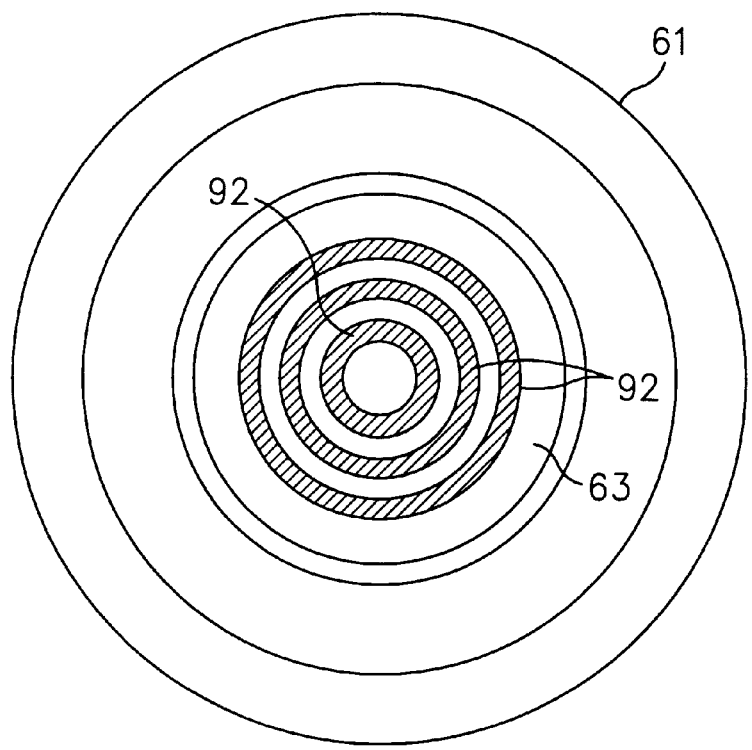
FIG. 9 is a top plan view of FIG. 8.

FIGS. 8 and 9 show an upper heating element 92 in muffle member 61 of furnace 60. Heating element 92 may be embedded in insulation member 63 to provide additional heat to the upper side of muffle member 61 and to reduce or eliminate any cold spots that may present in the upper section of the heating chamber. Heating element 92 is preferably comprised of a series of ring components or is in the form of a single spiral unit or other similar shape. As shown in FIG. 8, heating element 92 is positioned over and above firing platform 14 and 64 in FIGS. 1 and 5, respectively.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A furnace for heating a dental material comprising:
   an upper chamber having an upper heating element therein; and
   a movable work base having a lower heating element therein;

a linear rail;

a movable bracket coupled to the linear rail and movable vertically along the rail;

a platform bar coupled to the bracket;

a work base plate disposed on the platform bar for holding the work base;

a linear conductor assembly; and a brush holder assembly coupled to the platform bar, movable in the vertical direction, in contact with the linear conductor assembly, and linked to the heating elements.

2. The furnace of claim 1 wherein the linear conductor assembly comprises:

a mounting bar;

a series of insulator blocks mounted to the mounting bar; and a series of conductor rods mounted between the insulator blocks.

3. The furnace of claim 2 wherein the brush holder assembly comprises:

a series of spring loaded brushes, which maintain contact with the conductor rods.

4. The furnace of claim 1 wherein the dental material is selected from a facing, a veneer, a bridge, an inlay, or a crown.

5. The furnace of claim 1 wherein the upper chamber includes a second upper heating element located above the first upper heating element.

6. The furnace of claim 5 wherein the second upper heating element located above the first upper heating element comprises a single spiral unit positioned over and above the firing platform.

7. The furnace of claim 1 further comprising a vacuum atmosphere.

8. The furnace of claim 1 further comprising a cap positioned on the work base wherein the heating element is positioned substantially parallel to the top of the workbase.

9. The furnace of claim 1 further comprising a cap positioned on the work base wherein the heating element is positioned substantially parallel to the cap.

* * * * *